(12) United States Patent
Weng et al.

(10) Patent No.: US 10,590,209 B2
(45) Date of Patent: Mar. 17, 2020

(54) PROCESS AND CATALYST COMPOSITION FOR PRODUCING SELECTIVELY HYDROGENATED CONJUGATED DIENE POLYMER

(71) Applicant: TSRC Corporation, Kaohsiung (TW)

(72) Inventors: Kuoyu Weng, Kaohsiung (TW); Fengyu Yang, Kaohsiung (TW); Wenhsien Wen, Kaohsiung (TW); Ching Ting, Kaohsiung (TW); Ting-Yu Lee, Kaohsiung (TW)

(73) Assignee: TSRC Corporation, Kaohsiung (TW)

( * ) Notice: Subject to any disclaimer, the term of this patent is extended or adjusted under 35 U.S.C. 154(b) by 0 days.

(21) Appl. No.: 15/824,806

(22) Filed: Nov. 28, 2017

(65) Prior Publication Data

US 2018/0148520 A1    May 31, 2018

Related U.S. Application Data

(60) Provisional application No. 62/427,515, filed on Nov. 29, 2016.

(51) Int. Cl.

| | | |
|---|---|---|
| *C08F 8/04* | (2006.01) | |
| *C08F 4/76* | (2006.01) | |
| *B01J 31/14* | (2006.01) | |
| *B01J 31/06* | (2006.01) | |
| *B01J 31/22* | (2006.01) | |
| *C08C 19/02* | (2006.01) | |
| *C08F 36/06* | (2006.01) | |
| *C08F 36/08* | (2006.01) | |
| *C08F 210/02* | (2006.01) | |
| *C08F 210/06* | (2006.01) | |
| *C08K 5/56* | (2006.01) | |
| *C08L 9/06* | (2006.01) | |
| *C08L 71/08* | (2006.01) | |
| *C08F 4/6592* | (2006.01) | |
| *C08F 10/02* | (2006.01) | |
| *C07F 1/02* | (2006.01) | |
| *C07F 3/02* | (2006.01) | |
| *C08F 212/08* | (2006.01) | |

(52) U.S. Cl.
CPC ............... *C08F 4/76* (2013.01); *B01J 31/068* (2013.01); *B01J 31/143* (2013.01); *B01J 31/2295* (2013.01); *C08C 19/02* (2013.01); *C08F 8/04* (2013.01); *C08F 36/06* (2013.01); *C08F 36/08* (2013.01); *C08F 210/02* (2013.01); *C08F 210/06* (2013.01); *C08K 5/56* (2013.01); *C08L 9/06* (2013.01); *C08L 71/08* (2013.01); *B01J 2231/645* (2013.01); *B01J 2531/46* (2013.01); *C07F 1/02* (2013.01); *C07F 3/02* (2013.01); *C08F 4/65925* (2013.01); *C08F 10/02* (2013.01); *C08F 212/08* (2013.01); *C08F 2500/01* (2013.01); *C08F 2500/04* (2013.01)

(58) Field of Classification Search
CPC . C08C 19/02; C08F 8/04; B01J 31/068; B01J 31/143; B01J 31/2295
See application file for complete search history.

(56) References Cited

U.S. PATENT DOCUMENTS

| | | | | |
|---|---|---|---|---|
| 5,948,869 | A | * | 9/1999 | Vallieri .................. C08C 19/02 525/338 |
| 2007/0254802 | A1 | | 11/2007 | Lin et al. |
| 2013/0131287 | A1 | * | 5/2013 | Siraux ........................ B01J 8/10 526/64 |
| 2015/0353669 | A1 | | 12/2015 | Araki et al. |

FOREIGN PATENT DOCUMENTS

| | | |
|---|---|---|
| EP | 2316862 | 5/2011 |
| EP | 2716663 | 4/2014 |
| EP | 3381554 | 10/2018 |
| FR | 2900352 | 11/2007 |
| JP | H11-000563 | 1/1999 |
| KR | 10-024405 | 2/2000 |
| TW | 200710097 | 3/2007 |
| TW | 201431890 | 8/2014 |
| TW | 201726249 | 8/2017 |

OTHER PUBLICATIONS

TIPO; International Search Report issued by Taiwan Patent Office dated Sep. 19, 2018 in TW Application No. 10720861460.
JPO; Office Action issued by Japanese Patent Office dated Oct. 30, 2018 in JP Application No. 462216.
EPO; International Search Report dated Apr. 24, 2018 in EP Application No. 17001946.7.
Asandei et al., "Titanium-Mediated Living Radical Styrene Polymerizations. V. Cp2TiCl-Catalyzed Initiation by Epoxide Radical Ring Opening: Effect of Solvents and Additives," Journal of Polymer Science: Part A: Polymer Chemistry, vol. 44, pp. 2015-2026, (Feb. 2006).
Kosal et al., "Titanocene-Catalyzed Conjugate Reduction of α, β-Unsaturated Carbonyl Derivatives," Organic Letters 2010, vol. 12(1), pp. 44-47, (Dec. 2009).

* cited by examiner

*Primary Examiner* — Robert C Boyle
(74) *Attorney, Agent, or Firm* — Snell & Wilmer L.L.P.

(57) ABSTRACT

A catalyst composition for selectively hydrogenating a conjugated diene polymer in a homogeneous system is provided, wherein the conjugated diene polymer comprises a conjugated diene monomer or a combination of a conjugated diene monomer and a vinyl aromatic monomer. The catalyst composition includes the catalyst components of (a) a titanium compound; (b) an organometallic compound; and (c) an oligomer containing a polyglycol segment. The hydrogenated polymer produced using the catalyst composition and the method thereof is also provided.

7 Claims, 3 Drawing Sheets

PROCESS AND CATALYST COMPOSITION FOR PRODUCING SELECTIVELY HYDROGENATED CONJUGATED DIENE POLYMER

CROSS-REFERENCE TO RELATED APPLICATION

This application claims the right of priority based on U.S. Provisional Application No. 62/427,515, entitled "PROCESS AND CATALYST COMPOSITION FOR PRODUCING SELECTIVELY, PARTIALLY HYDROGENATED POLYMER," and filed on Nov. 29, 2016, which is incorporated herein by reference and assigned to the assignee hereof.

FIELD OF INVENTION

The present invention relates to a selectively hydrogenated conjugated diene polymer, particularly to the conjugated diene polymer being selectively hydrogenated using a catalyst composition containing a titanium compound.

BACKGROUND OF THE INVENTION

With great amount of unsaturated double bonds, non-hydrogenated conjugated diene polymers, such as copolymer/homopolymer of butadiene or isoprene or block/non-block copolymer of styrene-butadiene/isoprene, are usually advantageously applicable in crosslinking reactions like functionalization, grafting and vulcanization, etc. However, non-hydrogenated conjugated diene polymer is very unstable as being prone to degradation due to heat or oxidation in exposed of ultra-violet light or other unfavorable environment. Since that, in practice, those non-hydrogenated copolymers are improved by appropriate hydrogenation to largely reduce the amount of the unsaturated double bonds, so as to get good properties against unfavorable environment. Conventionally, catalysts used for hydrogenation of the conjugated diene polymer are classified into two types, heterogeneous catalysts and homogenous catalysts, wherein the homogeneous one has relatively higher activities by which the reaction can be conducted at mild pressure and temperature.

European Patent Appl. No. 2316862 discloses a method for hydrogenating the conjugated diene polymer in homogenous system using a catalyst composition containing a titanium compound and a fully substituted silane, wherein the fully substituted silane catalyst stabilizes other catalyst components in the catalyst composition and therefore enhances the catalytic activity. However, such catalyst composition still has shortcomings in its application. Therefore, there is a need to provide a new catalyst composition to fit the application requirements.

SUMMARY OF THE INVENTION

One aspect of the present invention is to provide a novel homogeneous hydrogenation catalyst composition which is stable to be easily stored and used for selectively hydrogenating a conjugated diene polymer. The conjugated diene polymer of the present invention includes homopolymers or copolymers polymerized of monomers containing conjugated diene. The so-called "selectively hydrogenated" or "selectively hydrogenating" means that the hydrogenation is mainly directed to the conjugated diene monomer.

In accordance with the present invention, the conjugated diene polymer can be successfully hydrogenated under a lower concentration of the catalyst composition. Therefore, the catalyst composition is very applicable for commercial mass production of the polymer. Due to the lower concentration of the catalyst composition, there is no need to remove the catalyst from the hydrogenated polymer, which greatly enhances economic efficiency. Furthermore, the hydrogenation of the present invention is very rapid and exhibits good reproducibility over a wide range of temperatures and pressures.

Other aspects and various embodiments included in the present invention to solve other problems and combined with the above aspects are disclosed in the following detailed descriptions.

DETAILED DESCRIPTION OF THE INVENTION

The preferred embodiments of the present invention will now be described in greater details. Descriptions of well-known components, materials and process techniques may be omitted so as to not unnecessarily obscure the embodiments of the invention.

The present invention provides a catalyst composition for selectively hydrogenating a conjugated diene polymer in a homogeneous system, wherein the conjugated diene polymer comprises a conjugated diene monomer or a combination of a conjugated diene monomer and a vinyl aromatic monomer, and the catalyst composition includes the catalyst components of (a) a titanium compound; (b) an organometallic compound; and (c) an oligomer containing a polyglycol segment. The present invention also provides a hydrogenated polymer produced using the catalyst composition and the method thereof.

Conjugated Diene Polymer

The term "conjugated diene polymer" of the present invention includes a homopolymer or a copolymer polymerized of monomers containing conjugated diene, wherein the polymer contains an active radical or a non-active radical at the terminal end of the molecule chain. The active radical is carbon free radical, anionic radical of carbon alkali metal ion or carbon cationic radical. The copolymer of a conjugated diene could be block, random and taper copolymers of two or more conjugated diene monomers, or block, random and taper copolymers of at least one conjugated diene monomer and at least one vinyl aromatic monomer. For example, copolymers of conjugated diene monomer and vinyl aromatic monomer can be one of the styrene-butadiene copolymer, the styrene-isoprene copolymer and the styrene-(butadiene/isoprene) copolymer. In preferred embodiments of the present invention, the weight average molecular weight (Mw) of the conjugated diene polymer is from 40,000 to 500,000, more preferably from 70,000 to 300,000, wherein the block copolymers composed of conjugated diene monomers and vinyl aromatic monomers are even more preferred.

Conjugated diene monomer suitable for use in the present invention could be a conjugated diene having carbon atoms from 4 to 12. Representative examples include 1,3-butadiene, isoprene, 2,3-dimethyl-1,3-butadiene, 1-methylbutadiene, 2-phenyl-1,3-butadiene, 1,3-pentadiene, 2-methyl-1,3-pentadiene, 1,3-hexadiene, 4,5-diethyl-1,3-octadiene, 3-butyl-1,3-octadiene, and a mixture thereof. 1,3-butadiene, isoprene and a mixture of butadiene and isoprene are more suitable for use in the present invention.

Vinyl aromatic monomers suitable for use in the present invention include styrene, tert-butylstyrene, α-methyl styrene, o-methyl styrene, p-methyl styrene, divinyl benzene, 1,1-diphenyl ethylene, vinyl naphthalene, N,N-dimethyl-p-aminoethylstyrene and N,N-diethyl-p-aminoethylstyrene, any combination thereof, preferably styrene. Representative examples of conjugated diene/vinyl aromatic copolymer include (1) butadiene/styrene copolymer, (2) isoprene/styrene copolymer and (3) butadiene/isoprene/styrene copolymer.

According to the present invention, prior to hydrogenation, conjugated diene polymer are produced by any of the methods known in the art, such as, anionic polymerization, cationic polymerization, free radical polymerization, complex polymerization, solution polymerization, and emulsion polymerization. It is preferable to use an organic lithium compound to serve as a catalyst initiator, thus obtaining a living polymer. The living polymer contains a carbon-lithium ion at the terminal end of the molecule chain. Therefore, when the monomer is added, polymerization could further proceed to lengthen the molecule chain. Examples of such organic lithium compounds are n-propyl lithium, iso-propyl lithium, n-butyl lithium, iso-butyl lithium, tert-butyl lithium, n-pentyl lithium, phenyl lithium, tolyl lithium, or a dilithio hydrocarbon selected from the group consisting of 1,4-dilithio-n-butane, 1,5-dilithio-pentane, 1,2-dilithio-diphenyl ethane, 1,4-dilithio-1,1,4,4-tetraphenyl butane, 1,3- or 1,4-bis(1-litho-3-methylpentyl)-benzene. The amount of such organic lithium compound may be suitably determined depending on the desired molecular weight of the polymer. In addition, a tertiary amine compound or ether compound could be added to the system for polymerizing the conjugated diene monomers in order to increase the vinyl structure content of the conjugated diene monomers. Such compounds suitable for use include general tertiary amine compounds, tetrahydrofuran and diethyl ether.

Hydrogenated Conjugated Diene Polymer

One purpose of the present invention is to hydrogenate the conjugated diene polymer as aforementioned using the catalyst composition to be described hereafter. Styrene-butadiene copolymer, styrene-isoprene copolymer, and styrene-(butadiene/isoprene) copolymer are suitable examples for hydrogenation, wherein the styrene-butadiene copolymer is hydrogenated into a styrene-ethylene-butylene-styrene (SEBS) block copolymer, the styrene-isoprene copolymer is hydrogenated into a styrene-ethylene-propylene-styrene (SEPS) block copolymer; and the styrene-(butadiene/isoprene) copolymer is hydrogenated into a styrene-ethylene-ethylene-propylene-styrene (SEEPS) block copolymer.

Hydrogenation Catalyst Composition

As aforementioned, the catalyst composition of the present invention includes the catalyst components of (a) a titanium compound; (b) an organometallic compound; and (c) an oligomer containing polyglycol segments, which are detailed as below.

(a) Titanium Compound

According to the preferred embodiments of the present invention, the catalyst component (a) is a titanium compound of a formula (I):

$R^1$ and $R^2$ are identical or different and are ones selected from the group consisting of hydrogen, halogen, $C_1$-$C_8$ alkyl, $C_1$-$C_8$ alkoxy, $C_6$-$C_{12}$ cycloalkyl, phenyl, phenoxy, $C_7$-$C_{10}$ arylalkoxy, $C_7$-$C_{10}$ arylalkyl, carboxy, —$CH_2$P(phenyl)$_2$, —$CH_2$Si($C_1$-$C_5$ alkyl)$_3$ and —P(phenyl)$_2$; and A is one selected from the group consisting of cyclopentadienyl, fluorenyl, indenyl and derivatives thereof, wherein $A_2$ can be two of the same A or different A.

For example, A could be $C_5R^6R^7R^8R^9R^{10}$ (cyclopentadienyl and derivatives thereof), wherein $R^6$, $R^7$, $R^8$, $R^9$, and $R^{10}$ could be the same or different and are ones selected from the group consisting of hydrogen, halogen, alkyl, aryl, carboxy, —$CH_2$P(phenyl)$_2$, —$CH_2$Si($C_1$-$C_5$ alkyl)$_3$ and —P(phenyl)$_2$.

According to the catalyst component (a) of the formula (I), a bis(cyclopentadienyl)titanium halide and a derivative thereof used suitably in the present invention could be bis(cyclopentadienyl)titanium difluorides, bis(cyclopentadienyl)titanium dichlorides, bis[(2,4-diphenylphosphinecyclopentadienyl)]titanium difluorides, bis[(2,4-dimethylphosphinecyclopentadienyl)]titanium difluorides, bis[(2,4-diphenylphosphinecyclopentadienyl)]titanium dichlorides, dimethoxy bis(cyclopentadienyl)titanium dichlorides, bis[(2,4-dimethylphosphinecyclopentadienyl)]titanium dichlorides, bis(cyclopentadienyl)titanium dibromides, bis[(2,4-diphenylphosphinecyclopentadienyl)]titanium dibromides, bis[(2,4-dimethylphosphinecyclopentadienyl)]titanium dibromides, bis(ethyl cyclopentadienyl)titanium dichlorides, bis(n-propylcyclopentadienyl)titanium dichlorides, bis(n-butylcyclopentadienyl)titanium dichlorides, bis(2-ethylhexylcyclopentadienyl)titanium dichlorides, (dimethylsilylene)-bis($\eta^5$-2,4-cyclopentadien-1-ylidene) or (ethylene)-bis($\eta^5$-2,4-cyclopentadien-1-ylidene).

According to the catalyst component (a) of the formula (I), an organic carbohydrate of a bis(cyclopentadienyl)titanium and a derivative thereof used suitably in the present invention could be bis(cyclopentadienyl)titanium dimethyl, bis(cyclopentadienyl)titanium dimethoxy, bis(2,4-diphenylphosphinecyclopentadienyl)titanium dimethoxy, bis(2,4-dimethylphosphinecyclopentadienyl)titanium dimethoxy, bis(cyclopentadienyl)titanium diethoxy, bis(2,4-diphenylphosphinecyclopentadienyl)titanium diethoxy, bis(2,4-dimethylphosphinecyclopentadienyl)titanium diethoxy, bis(2,4-diphenylphosphinecyclopentadienyl)titanium diphenoxy or bis(2,4-dimethylphosphinecyclopentadienyl)titanium diphenoxy.

According to the catalyst component (a) of the formula (I), a bifluorenyl titanium halide, a biindenyl titanium halide and a derivative thereof used suitably in the present invention could be bis(1-fluorenyl)titanium dichlorides, bis(1-indenyl)titanium dichlorides, bis(dimethoxyfluorenyl)titanium dichlorides, bis(fluorenyl)titanium difluorides, bis (indenyl)titanium difluorides, bis(dimethoxylfluorenyl) titanium difluorides, bis(fluorenyl)titanium dibromides, bis (indenyl)titanium dibromides, bis(dimethoxylfluorenyl) titanium or bis(indenyl)titanium dibromides.

According to the catalyst component (a) of the formula (I), an organic carbohydrate could be bifluorenyl titanium, biindenyl titanium and a derivative thereof used suitably in the present invention could be bis(fluorenyl)titanium dimethyl, bis(fluorenyl)titanium dimethoxy, bis(indenyl)titanium dimethoxy, bis(dimethoxylfluorenyl)titanium dimethoxy, bis(indenyl)titanium dimethoxy, bis(fluorenyl) titanium dimethanol, bis(indenyl)titanium dimethanol, bis (dimethoxylfluorenyl)titanium dimethanol, bis(indenyl) titanium dimethanol, bis(fluorenyl)titanium diphenoxy, bis (dimethoxylfluorenyl)titanium diphenoxy or bis(indenyl) titanium diphenoxy.

The derivative here indicates that there is a substituent on the indenyl, fluorenyl, or cyclopentadienyl ring, and the substituent could be one or more from methyl, methoxy, p-tert-butylphenyl, pentafluorophenyl, trifluorophenyl, difluorophenyl, or 3,5-(tert-butyl)-4-methoxyphenyl. A preferred example of the catalyst component (a) is bis(cyclopentadienyl)titanium dichloride.

(b) Organometallic Compound

According to the preferred embodiments of the present invention, the catalyst component (b) is an organometallic compound including $R^3Li$, $R^3R^4Mg$, or $R^3R^4R^5Al$, wherein the $R^3$ is one selected from the group consisting of hydrogen, $C_1$-$C_{12}$ alkyl, $C_1$-$C_{12}$ alkoxy, $C_6$-$C_{12}$ aryl and $C_6$-$C_{12}$ alkoxy, and the $R^4$ and $R^5$ are identical or different and are ones selected from the group consisting of hydrogen, halogen, $C_1$-$C_{12}$ alkyl, and $C_6$-$C_{12}$ aryl.

According to the catalyst component (b) of present invention, an example of organic aluminum compound could be tri-methyl aluminum, tri-ethyl aluminum, tri-n-propyl aluminum, tri-isopropyl aluminum, tri-butyl aluminum, tri(sec-butyl)aluminum, tri(isobutyl)aluminum, tri(n-pentyl)aluminum, tri(isopentyl)aluminum, tri(n-hexyl)aluminum, tri (isohexyl)aluminum, tri(1-methylpentyl)aluminum, tri(2,5-dimethyloctyl)aluminum, tri(2,6-dimethyloctyl)aluminum, tri(2-ethylhexyl)aluminum, triphenyl aluminum, diethyl aluminum chloride, ethyl aluminum dichloride, tripropyl aluminum chloride, dibutyl aluminum chloride, diisobutyl aluminum chloride, or butyl aluminum dichloride, wherein tri-ethyl aluminum, tri-isopropyl aluminum, tri-butyl aluminum, tri(isobutyl)aluminum, or diethyl aluminum chloride are preferred.

According to the catalyst component (b) of present invention, an example of organic lithium compound could be n-propyl lithium, iso-propyl lithium, n-butyl lithium, iso-butyl lithium, tert-butyl lithium, n-pentyl lithium, phenyl lithium, tolyl lithium and a dilithio hydrocarbon selected from the group consisting of 1,4-dilithio-n-butane, 1,5-dilithio-pentane, 1,2-dilithio-diphenyl ethane, 1,4-dilithio-1, 1,4,4-tetraphenyl butane, 1,3- or 1,4-bis(1-litho-3-methylpentyl)-benzene.

According to the present invention, the organic magnesium of the catalyst component (b) is one of Grignard compound and the dialkyl compound of magnesium. For commercial application, there are many magnesium compounds existing in a type of using an organic magnesium compound to dissolve in an inert aliphatic hydrocarbon. There are examples including bis-n-butyl magnesium, bis-tert-butyl magnesium, bis-isobutyl magnesium, bis-n-propyl magnesium, bis-isopropyl magnesium, bisoctyl magnesium, biscyclohexyl magnesium, bis-2-ethylhexyl magnesium, n-butyl-isobutyl magnesium, n-butyloctyl magnesium, n-butyl-2-ethylhexyl magnesium and a combination thereof.

(c) Oligomer

According to the preferred embodiments of the present invention, the catalyst component (c) is an oligomer containing a polyglycol segment. It has been surprisingly discovered that the functional group of polyglycol together with the catalyst components (a) and (b) can form a stable co-catalyst system, particularly in avoiding losing activity of titanium compound catalyst at an early stage, more particularly in providing a more preferable stability when taking the oligomer containing a polyglycol segment as the catalyst component (c). Examples of the catalyst component (c) include, for example, homopolymers composed of polyglycol or block typed or random typed copolymers composed of different units of polyglycol monomers which have a molecular weight in the range of oligomers, or any other oligomers or grafted oligomers containing a polyglycol segment. The oligomer according to the preferred examples of the present invention is a polymer with a low number of repeat units, which has a weight average molecular weight (Mw) from 400 to 10,000, more preferred from 400 to 4,000. The preferred examples are homopolymer of ethylene glycol or propylene glycol; a block copolymer of ethylene glycol and propylene glycol, such as poly(ethylene glycol)-block-poly(propylene glycol) (PEG-b-PPG) or a poly(ethylene glycol)-block-poly(propylene glycol)-block-poly(ethylene glycol) (PEG-b-PPG-b-PEG); a random copolymer of ethylene glycol and propylene glycol (PEG-ran-PPG); and poly(dimethylsiloxane-b-ethylene oxide), methyl terminated (PDMS-PEG).

Preparation of catalyst components (a), (b) and (c) should be conducted in inert gas and low water content. The inert gas refers to helium, neon, nitrogen and the like, which will not participate in hydrogenation. Air, oxygen or high water content atmosphere will oxidize or decompose the hydrogenation catalysts, causing reduced activity in catalysts. In the condition under which the catalyst components are pre-mixed, the temperature is preferably ranged from 0° C. to 250° C. The activity of catalyst would be reduced at an over higher temperature. The hydrogenating ability would be disappeared at an over lower temperature even though the catalyst does not lose its activity.

Method for Selectively Hydrogenating the Conjugated Diene Polymer

Since the catalyst composition of the present invention tends to selectively hydrogenate "conjugated diene monomer," the hydrogenation rate for the unsaturated double bonds in the vinyl aromatic monomers are far less than the hydrogenation rate for the unsaturated double bonds in the conjugated diene monomers when hydrogenating the copolymer composed of the conjugated diene monomer and the vinyl aromatic monomer. In preferred embodiments of the present invention, the hydrogenation rate for the unsaturated double bonds in the conjugated diene monomers is at least 70%, more preferred at least 85%, even more preferred at least 95%; and the hydrogenation rate for the unsaturated double bonds in the vinyl aromatic monomers is less than 5%, more preferred less than 2%.

The hydrogenation of the present invention involves bringing the conjugated diene polymer in one of an inert organic solvent and an inert organic solvent which includes a portion of ether and amine polar compound into contact with hydrogen in the presence of the hydrogenation catalyst composition of the present invention. Thus, the unsaturated double bonds in the conjugated diene units of the conjugated diene polymer are selectively hydrogenated. Specifically, for example, gaseous hydrogen is introduced into the conjugated diene polymer. Then, stirring is conducted to completely contact the hydrogen and conjugated diene polymer. Hydrogenation could be conducted by a batch or continuous methods. The hydrogenation reactor of the present invention could be a tank reaction, a loop reactor, a column reactor or a continuously stirred tank reactor (CSTR).

The hydrogenation catalyst composition of the present invention includes hydrogenation catalyst components (a), (b) and (c) as mentioned above. The addition sequence of the hydrogenation catalyst components (a), (b) and (c) is not limited. For example, the catalyst component (c) could be first added to the polymer solution whose activity has been terminated, and then a mixed solution of catalyst compositions (a) and (b) are added. Alternatively, the catalyst component (c) could be first added to the polymer solution whose activity has not been terminated, followed by a catalyst component (a) solution and a catalyst component (b) solution, respectively. After all the catalyst components are added to the polymer, the polymer is kept at the inert gas atmosphere. The catalyst composition still has relatively good activity even after storage for a long time. Therefore, the catalyst composition of the present invention is very suitable for the requirement of industrial mass production.

According to the present invention, the inert organic solvent to dissolve the hydrogenation catalyst composition and the conjugated diene polymer could be a linear or branched hydrocarbon compound such as pentane, hexane, heptane, octane and the like; or a cyclic hydrocarbon compound such as cyclohexane, cycloheptane, and methylheptane. Cyclohexane and n-hexane are the most suitable example. Alternatively, the inert organic solvent could be aromatic hydrocarbon such as benzene, toluene, xylene and ethylbenzene.

Regarding the usage amount, based on 100 g of the conjugated diene polymer the hydrogenation catalyst component (a) is present in an amount of 0.0001 mmole to 50 mmole, preferably 0.002 mmole to 10 mmole, more preferably 0.01 mmole to 5 mmole. Over higher usage amount of the catalyst component (a) causes more catalyst residue which increases more side reactions with antioxidant and thus turns the products to yellow, while over lower usage amount of the catalyst component (a) reduces the hydrogenation efficiency.

Preferably, the molar ratio of the hydrogenation catalyst component (a) to the hydrogenation catalyst component (b) is 0.01 to 50, more preferably 0.1 to 10, even more preferably 0.2 to 5. If the molar ratio of the hydrogenation catalyst component (a) to the hydrogenation catalyst component (b) is higher than 50, the hydrogenation catalyst component (b) cannot efficiently activate and stable the hydrogenation catalyst component (a), and thus, hydrogenation performance is undesired. If the molar ratio of the hydrogenation catalyst component (a) to the hydrogenation catalyst component (b) is lower than 0.01, the amount of the hydrogenation catalyst component (b) is probably too much and thus the undesired secondary reaction easily occurs, which reduces the hydrogenation efficiency and results in a need to remove the catalyst composition from the product.

Preferably, the molar ratio of the hydrogenation catalyst component (c) to the hydrogenation catalyst component (a) is 0.1 to 10, more preferably 0.5 to 5, even more preferably 1 to 4. If the molar ratio of the hydrogenation catalyst component (c) to the hydrogenation catalyst component (a) is less than 0.1, the hydrogenation catalyst component (c) does not reliably stabilize the hydrogenation catalyst system and thus the catalyst composition loses its activity. If the molar ratio of the hydrogenation catalyst component (c) to the hydrogenation catalyst component (a) is higher than 10, the hydrogenation catalyst system is too stable to proceed with hydrogenation.

The hydrogenation reaction of the present invention could be conducted at a temperature of 0° C. to 250° C. If the reaction temperature is lower than 0° C., the hydrogenation reaction cannot happen because it cannot force the catalyst composition to overcome the activation energy. If the reaction temperature is higher than 250° C., the catalyst composition will be decomposed and deactivated, thus decreasing the catalytic activity.

The hydrogenation could be conducted preferably at a hydrogen pressure from 0.1 kg/cm$^2$ to 150 kg/cm$^2$, more preferably 1 kg/cm$^2$ to 100 kg/cm$^2$, most preferably 1 kg/cm$^2$ to 50 kg/cm$^2$. When the hydrogen pressure is less than 0.1 kg/cm$^2$, the reaction rate may be not obvious. When the hydrogen pressure is higher than 150 kg/cm$^2$, the hydrogenation will rapidly stop. The catalyst amount could be decreased by increasing the hydrogen pressure. In order to decrease the catalyst amount, it is preferable to conduct hydrogenation at higher hydrogen pressure.

According to the present invention, the hydrogenation time could be several seconds to 40 hours. Suitable range could be adjusted by the reaction conditions such as the ratio of the catalysts, hydrogen pressure, and hydrogenation temperature.

To hydrogenate the conjugated diene/vinyl aromatic copolymer using the catalyst composition of the present invention, at least 70%, more preferably at least 85%, even more preferably at least 95%, of the unsaturated double bonds in the conjugated diene monomers can be hydrogenated. In contrast, lower than 5%, and even lower than 2%, of the double bonds in the vinyl aromatic monomers (aromatic ring such as benzene ring) can are hydrogenated. That is to say, the catalyst composition of the present invention has relatively good catalytic selectivity. The hydrogenation rate could be measured by $^1$H-NMR spectrum analysis as conducted by person skilled in the art, which could be referred to U.S. Pat. No. 5,017,660.

The polymer solution obtained from hydrogenation using the hydrogenation catalyst composition of the present invention could be coagulated by adding a polar solvent. Such polar solvent is a poor solvent for the hydrogenated polymer, such as methanol or acetone. Or, alternatively, the hydrogenated polymer solution could be poured into hot water, stirred, and then distilled for separation. Or, the hydrogenated polymer solution could be directly heated to evaporate the solvent for separation.

According to the present invention, the conjugated diene polymer could be successfully hydrogenated using a small amount of a hydrogenation catalyst composition with relatively high activity. Since the catalyst composition concentration is very low, most catalyst is separated from the polymer or decomposes during the polymer separation procedure. Therefore, there is no need to wash or remove the catalyst from the hydrogenated polymer, greatly enhancing economic efficiency.

A feature of the catalyst composition of the present invention is that the catalyst component (c) could combine with other catalysts to stabilize other catalyst components and enhance the catalytic activity thereof. Therefore, when the catalyst composition of the present invention is added to the conjugated diene polymer, it could be stored for a period of time in the inert gas atmosphere, generally more than 1 hour, still maintaining good catalytic activity and reproducibility. Another feature is that the catalyst composition of the present invention has high hydrogenation activity at a higher temperature. In addition, the catalyst composition of the present invention will not lose the catalytic activity due to high hydrogenation reaction heat. Therefore, it is very suitable for commercial mass production.

Specific preferred embodiments of the present invention have been described in the detailed description below. The description is not intended to limit the invention. Persons skilled in the art should understand the spirit and scope of the invention is as stated in the claims.

Example 1 (Comparative Example without Catalyst Component (c))

Figure 1:
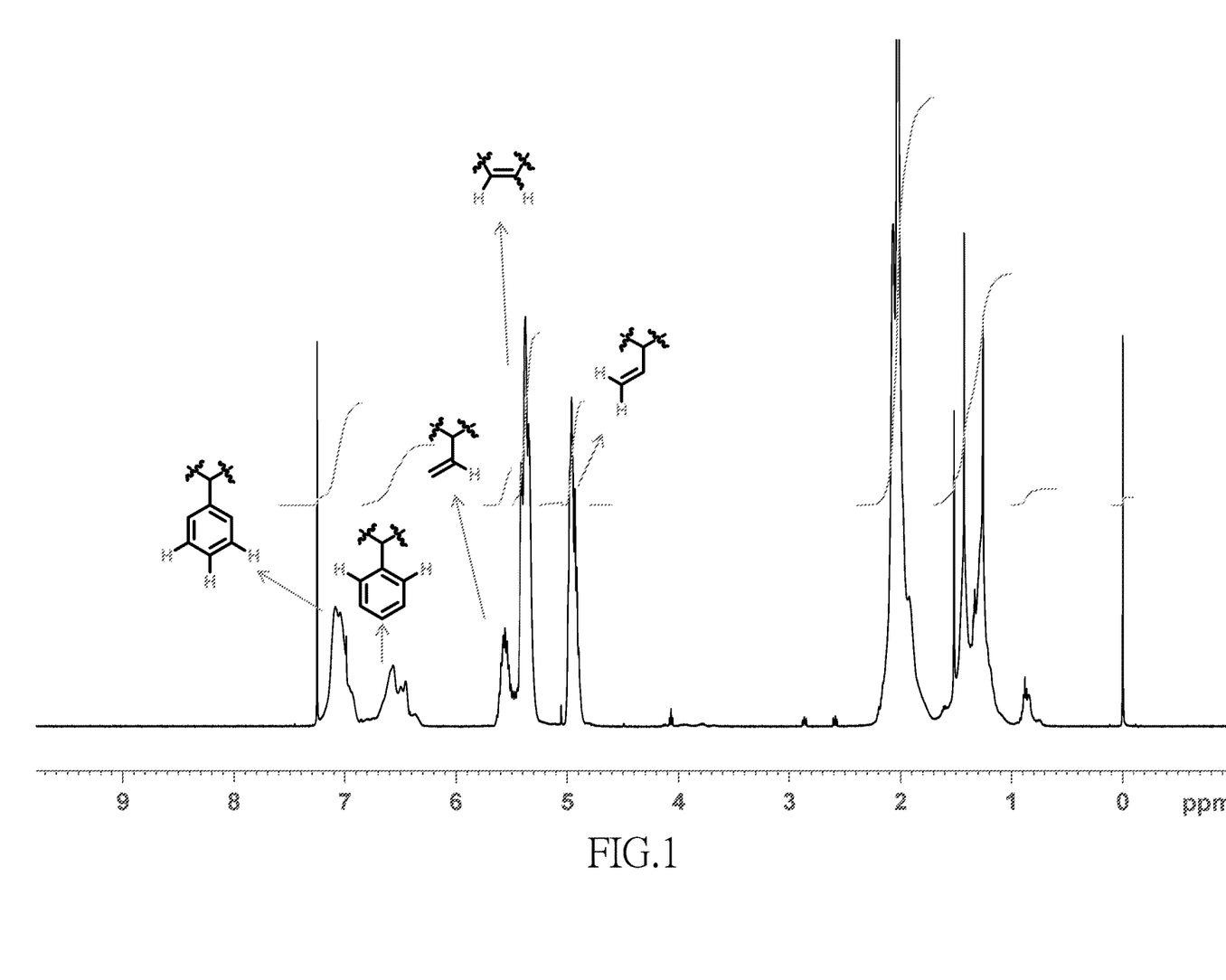
FIG. 1 shows the $^1$H-NMR spectrum of the non-hydrogenated block copolymer in accordance with Example 1 of the present invention.
Figure 2:
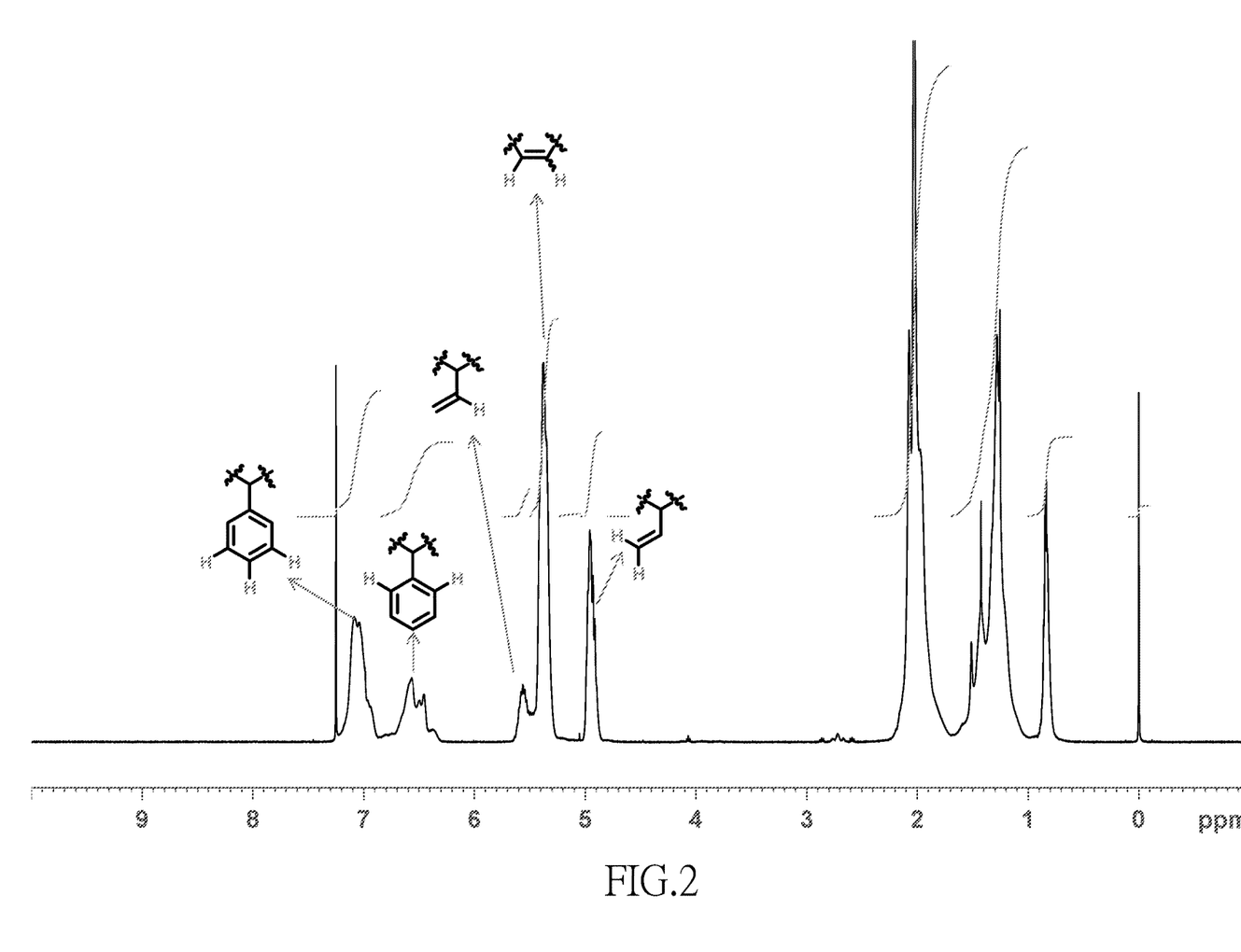
FIG. 2 shows the $^1$H-NMR spectrum of the hydrogenated block copolymer in accordance with Example 1 of the present invention.

4300 g of cyclohexane, 15.6 mmoles of n-butyl lithium and 139 mmoles of tetrahydrofuran (THF) were charged in 10 L of a heater equipped with a stirrer. Then, 93 g of styrene was added and the polymerization was conducted at 45° C. Then, 400 g of 1,3 butadiene and 93 g of styrene were added to the reaction system and the reaction mixture was further polymerized to an SBS (styrene-butadiene-styrene) tri-block copolymer (solid content=12%, Mw=75,000), which is non-hydrogenated. FIG. 1 shows the $^1$H-NMR spectrum of the non-hydrogenated block copolymer in accordance with Example 1 of the present invention. 1000 g of the polymer solution of non-hydrogenated SBS tri-block copolymer prepared from Example 1 was transferred to a pressure-resistant hydrogenation vessel and maintained in the nitrogen atmosphere. Separately, 0.25 mmoles of bis(cyclopentadienyl) titanium dichloride (the catalyst component (a)) and 0.5 mmoles of triisobutyl aluminum (the catalyst component (b) were mixed in 10 ml of cyclohexane. In the example the catalyst component (c) is not used. The above catalyst solution was added into the non-hydrogenated SBS tri-block copolymer wherein the mole ratio of catalyst components (a):(b):(c) is 1:2:0. Hydrogen was fed in under a pressure of 25 kg/cm$^2$ to undergo hydrogenation starting at 80° C. and reaching up to around 90° C. After around 60 mins of reaction time, the hydrogenated SBS triblock copolymer was obtained. FIG. 2 shows the $^1$H-NMR spectrum of the hydrogenated block copolymer in accordance with Example 1 of the present invention. In absence of the catalyst component (c), the hydrogenated block copolymer of Example 1 has a hydrogenation rate of only 17% for the unsaturated double bonds of the conjugated diene monomer.

Examples 2 to 12 exemplify the catalyst compositions of the present invention.

Example 2

4300 g of cyclohexane, 15.6 mmoles of n-butyl lithium and 139 mmoles of tetrahydrofuran (THF) were charged in 10 L of a heater equipped with a stirrer. Then, 93 g of styrene was added and the polymerization was conducted at 45° C. Then, 400 g of 1,3 butadiene and 93 g of styrene were added to the reaction system and the reaction mixture was further polymerized to an SBS (styrene-butadiene-styrene) tri-block copolymer (solid content=12%, Mw=75,000). 1000 g of the polymer solution of SBS tri-block copolymer was transferred to a pressure-resistant hydrogenation vessel and maintained in the nitrogen atmosphere. 0.25 mmoles of oligomer polypropylene glycol (the catalyst component (c)) having a weight average molecular weight (Mw) 700 was dissolved in 10 ml of cyclohexane. Separately, 0.25 mmoles of bis(cyclopentadienyl)titanium dichloride (the catalyst component (a)) and 0.5 mmoles of triisobutyl aluminum (the catalyst component (b)) were mixed in 10 ml of cyclohexane. The above catalyst solution was added into the non-hydrogenated SBS tri-block copolymer wherein the mole ratio of catalyst components (a):(b):(c) is 1:2:1. Hydrogen was fed in under a pressure of 25 kg/cm$^2$ to undergo hydrogenation starting at 80° C. and reaching up to around 110° C. After around 60 mins of reaction time, the hydrogenated SBS triblock copolymer was obtained. The hydrogenated block copolymer of Example 2 has a hydrogenation rate of 98% for the unsaturated double bonds of the conjugated diene monomer.

Figure 3:
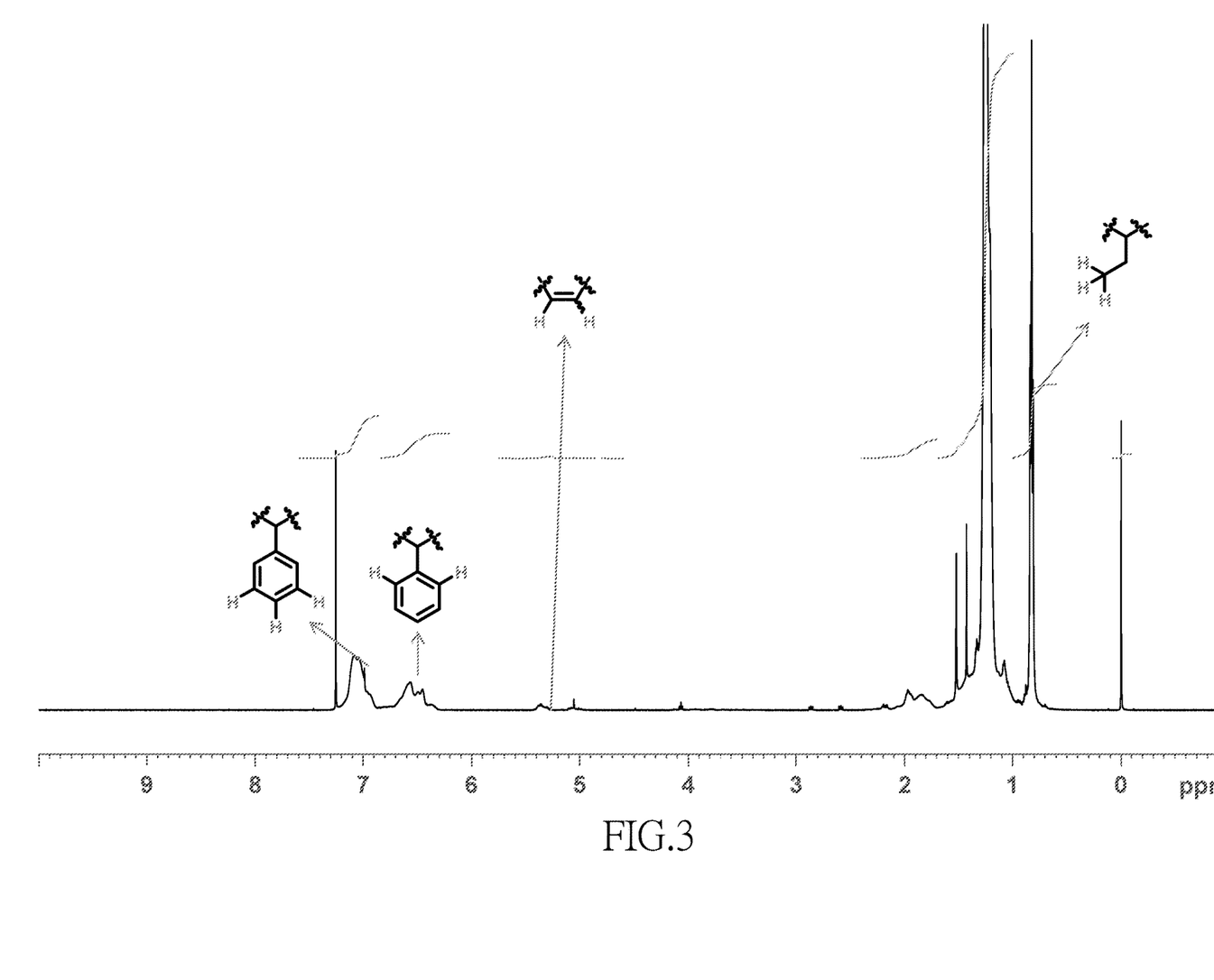
FIG. 3 shows the $^1$H-NMR spectrum of the hydrogenated block copolymer in accordance with Example 3 of the present invention.

Examples 3 to 6 were conducted under various experimental conditions shown in Table I in the same manner as in Example 2. Examples 2-6 mainly demonstrate that under the hydrogen pressure between 25 kg/cm$^2$ to 35 kg/cm$^2$ and the molar ratio ranged from 1:2:1 to 1:2:4 of the catalyst components (a):(b):(c), the hydrogenated SBS triblock copolymers having a hydrogenation rate of 95% to 98% for the unsaturated double bonds of the conjugated diene monomer are obtained. FIG. 3 shows the $^1$H-NMR spectrum of the hydrogenated block copolymer in accordance with Example 3 of the present invention.

Examples 7 to 8 were conducted under various experimental conditions shown in Table I in the same manner as in Example 2. Examples 3, 7 and 8 mainly demonstrate that hydrogenating the SBS triblock copolymer with weight average molecular weight (Mw) in the range of 75,000 to 260,000 under the same molar ratio 1:2:2 of the catalyst components (a):(b):(c), the hydrogenated SBS triblock copolymers having a hydrogenation rate of 95% to 98% for the unsaturated double bonds of the conjugated diene monomer are obtained.

Examples 9 to 11 were conducted under various experimental conditions shown in Table I in the same manner as in Example 2. Examples 3 and 9-11 mainly demonstrate that under the same molar ratio 1:2:2 of the catalyst components (a):(b):(c) wherein the catalyst component (c) is oligomer PPG (poly propylene glycol) or PEG (poly ethyl glycol) having a weight average molecular weight (Mw) ranged between 400 to 1000, the hydrogenated SBS triblock copolymers having a hydrogenation rate of 97% to 98% for the unsaturated double bonds of the conjugated diene monomer are obtained.

Example 12 was conducted under various experimental conditions shown in Table I in the same manner as in Example 2. Example 12 mainly demonstrate that under the molar ratio 1:2:2 of the catalyst components (a):(b):(c) wherein the catalyst component (c) is oligomer PDMS-PEG (Poly(dimethylsiloxane-b-ethylene oxide), methyl terminated) having a weight average molecular weight (Mw) 600, the hydrogenated SBS triblock copolymer having a hydrogenation rate of 97% for the unsaturated double bonds of the conjugated diene monomer is obtained. Example 12 shows that the oligomer containing a polyglycol segment is suitable for use in the catalyst component (c) of the present invention.

FIG. 1 to FIG. 3 show the $^1$H-NMR spectrums of the hydrogenated and non-hydrogenated SBS triblock copolymers for analysis of the detailed structure. By observing the adsorption peaks at the range of 4.5 to 6 ppm in the figures, FIG. 1 indicates that the butadiene group on the SBS triblock copolymer are not hydrogenated; FIG. 2 indicates that few of the butadiene group on the SBS triblock copolymer are hydrogenated; and FIG. 3 indicates that most of the butadiene group on the SBS triblock copolymer are hydrogenated. The adsorption peaks at the range of 6.0 to 7.5 ppm indicates the styrene group on the SBS triblock copolymer.

TABLE I

| Ex. | polymer | Catalyst Composition | a:b:c mole ratio | Start Temp | H$_2$ Pressure kg/cm$^2$ | Hydrogenation time (min) | Hydrogenation rate of conjugated diene monomer | Hydrogenation rate of vinyl aromatic monomer |
|---|---|---|---|---|---|---|---|---|
| 1 | SBS (Mw: 75,000) | (a) bis(cyclopentadienyl)titanium dichlorides (b) triisobutyl aluminum (c) PPG (Mw: 700) | 1:2:0 | 80° C. | 25 | 60 | 17% | <1% |
| 2 | SBS (Mw: 75,000) | (a) bis(cyclopentadienyl)titanium dichlorides (b) triisobutyl aluminum (c) PPG (Mw: 700) | 1:2:1 | 80° C. | 25 | 60 | 98% | <1% |
| 3 | Same as Ex. 2 | Same as Ex. 2 | 1:2:2 | 80° C. | 25 | 60 | 98% | <1% |
| 4 | Same as Ex. 2 | Same as Ex. 2 | 1:2:3 | 80° C. | 25 | 60 | 96% | <1% |
| 5 | Same as Ex. 2 | Same as Ex. 2 | 1:2:4 | 80° C. | 25 | 60 | 95% | <1% |
| 6 | Same as Ex. 2 | Same as Ex. 2 | 1:2:2 | 80° C. | 35 | 40 | 98% | <1% |
| 7 | SBS (Mw: 95,000) | Same as Ex. 2 | 1:2:2 | 80° C. | 25 | 60 | 98% | <1% |
| 8 | SBS (Mw: 260,000) | Same as Ex. 2 | 1:2:2 | 80° C. | 25 | 60 | 95% | <1% |
| 9 | SBS (Mw: 95,000) | (a) bis(cyclopentadienyl)titanium dichlorides (b) triisobutyl aluminum (c) PPG (Mw: 400) | 1:2:2 | 80° C. | 25 | 60 | 98% | <1% |
| 10 | Same as Ex. 9 | (a) bis(cyclopentadienyl)titanium dichlorides (b) triisobutyl aluminum (c) PPG (Mw: 1000) | 1:2:2 | 80° C. | 25 | 60 | 97% | <1% |
| 11 | Same as Ex. 9 | (a) bis(cyclopentadienyl)titanium dichlorides (b) triisobutyl aluminum (c) PEG (Mw: 600) | 1:2:2 | 80° C. | 25 | 60 | 97% | <1% |
| 12 | Same as Ex. 9 | (a) bis(cyclopentadienyl)titanium dichlorides (b) triisobutyl aluminum (c) PDMS-PEG (Mw: 600) | 1:2:2 | 80° C. | 25 | 60 | 97% | <1% |

While the invention has been described by way of examples and in terms of preferred embodiments, it would be apparent to those skilled in the art to make various equivalent replacements, amendments and modifications in view of specification of the invention. Therefore, the scope of the appended claims should be accorded the broadest interpretation so as to encompass all such replacements, amendments and modifications without departing from the spirit and scope of the invention.

The invention claimed is:

1. A catalyst composition for selectively hydrogenating a conjugated diene polymer comprising a conjugated diene monomer or a combination of a conjugated diene monomer and a vinyl aromatic monomer, the catalyst composition comprising components of:
   (a) a titanium compound of a formula (I), (I)

wherein:
R$^1$ and R$^2$ are identical or different and are ones selected from the group consisting of hydrogen, halogen, C$_1$-C$_8$ alkyl, C$_1$-C$_8$ alkoxy, C$_6$-C$_{12}$ cycloalkyl, phenyl, phenoxy, C$_7$-C$_{10}$ arylalkoxy, C$_7$-C$_{10}$ arylalkyl, carboxy, —CH$_2$P(phenyl)$_2$, —CH$_2$Si(C$_1$-C$_5$ alkyl)$_3$ and —P(phenyl)$_2$; and A is one selected from the group consisting of cyclopentadienyl, fluorenyl, indenyl and derivatives thereof, wherein A$_2$ can be two of the same A or different A;
   (b) an organometallic compound selected from the group consisting of R$^3$Li, R$^3$R$^4$Mg and R$^3$R$^4$R$^5$Al, wherein said R$^3$ is one selected from the group consisting of hydrogen, C$_1$-C$_{12}$ alkyl, C$_1$-C$_{12}$ alkoxy, C$_6$-C$_{12}$ aryl and C$_6$-C$_{12}$ alkoxy, and said R$^4$ and R$^5$ are identical or different and are ones selected from the group consisting of hydrogen, halogen, C$_1$-C$_{12}$ alkyl and C$_6$-C$_{12}$ aryl; and
   (c) an oligomer containing a polyglycol segment, wherein the catalyst component (c) has a weight average molecular weight (Mw) from 400 to 10,000 and a molar ratio of the catalyst component (a) to the catalyst component (b) is from 0.01 to 50.

2. The catalyst composition according to claim 1, wherein the catalyst component (c) is a homopolymer of ethylene glycol or propylene glycol, a block copolymer of ethylene glycol and propylene glycol, or a random copolymer of ethylene glycol and propylene glycol.

3. The catalyst composition according to claim 2, wherein the catalyst component (c) is a poly(ethylene glycol)-block-poly(propylene glycol) (PEG-b-PPG) or a poly(ethylene glycol)-block-poly(propylene glycol)-block-poly(ethylene glycol) (PEG-b-PPG-b-PEG).

4. The catalyst composition according to claim 1, wherein the catalyst component (c) is a poly(dimethylsiloxane-b-ethylene oxide), methyl terminated (PDMS-PEG).

5. The catalyst composition according to claim 1, wherein a molar ratio of the catalyst component (c) to the catalyst component (a) is from 0.1 to 10.

6. The catalyst composition according to claim 1, wherein the catalyst composition comprises the conjugated diene polymer and the catalyst component (a) is present in an amount of 0.0001 mmole to 50 mmole based on 100 g of the conjugated diene polymer.

7. The catalyst composition according to claim 1, wherein the catalyst composition can hydrogenate the conjugated diene copolymer to achieve a hydrogenation rate of at least 70% for unsaturated double bonds of the conjugated diene monomers; or a hydrogenation rate of at least 70% for unsaturated double bonds of the conjugated diene monomers and a hydrogenation rate of less than 5% for unsaturated double bonds of the vinyl aromatic monomers.

\* \* \* \* \*